US005706820A

United States Patent [19]

Hossack et al.

[11] Patent Number: 5,706,820

[45] Date of Patent: Jan. 13, 1998

[54] ULTRASONIC TRANSDUCER WITH REDUCED ELEVATION SIDELOBES AND METHOD FOR THE MANUFACTURE THEREOF

[75] Inventors: John A. Hossack, Palo Alto; Samuel Moss Howard, Mountain View, both of Calif.

[73] Assignee: Acuson Corporation, Mountain View, Calif.

[21] Appl. No.: 482,147

[22] Filed: Jun. 7, 1995

[51] Int. Cl.[6] .......... A61B 8/00

[52] U.S. Cl. .......... 128/662.03; 29/25.35

[58] Field of Search .......... 128/662.03, 661.01; 367/140; 29/25.35; 310/334–336

[56] References Cited

U.S. PATENT DOCUMENTS

| | | | |
|---|---|---|---|
| 4,217,684 | 8/1980 | Brisken | 29/25.35 |
| 4,425,525 | 1/1984 | Smith | 310/336 |
| 4,460,841 | 7/1984 | Smith | 310/334 |
| 4,518,889 | 5/1985 | 'T Hoen | 310/357 |
| 5,044,053 | 9/1991 | Kopel | 29/25.35 |
| 5,099,459 | 3/1992 | Smith | 128/662.03 X |
| 5,115,810 | 5/1992 | Watanabe et al. | 128/662.03 |
| 5,167,231 | 12/1992 | Matsui | 128/662.03 |
| 5,371,717 | 12/1994 | Bolorforsh | 367/140 |
| 5,402,791 | 4/1995 | Saitoh et al. | 128/662.03 |
| 5,492,134 | 2/1996 | Souquet | 128/662.03 |
| 5,546,946 | 8/1996 | Souquet | 128/662.03 |
| 5,553,035 | 9/1996 | Seyed-Bolorforosh et al. | 128/662.03 |

FOREIGN PATENT DOCUMENTS

| | | | |
|---|---|---|---|
| 5168637 | 7/1993 | Japan | 128/662.03 |
| 6014927 | 1/1994 | Japan | 128/660.01 |

*Primary Examiner*—Francis Jaworski
*Attorney, Agent, or Firm*—Brinks Hofer Gilson & Lione

[57] ABSTRACT

An ultrasound transducer and the method for the manufacture thereof which is designed to reduce the generation of elevational sidelobes. At least one kerf is formed in each end region of a body of piezoelectric material. The kerfs define therebetween a center region formed solely of piezoelectric material. The kerfs are filled with a second material.

23 Claims, 8 Drawing Sheets

L7 GEOMETRY WITH NO IMPROVEMENTS

FIG.6
FIG.6A
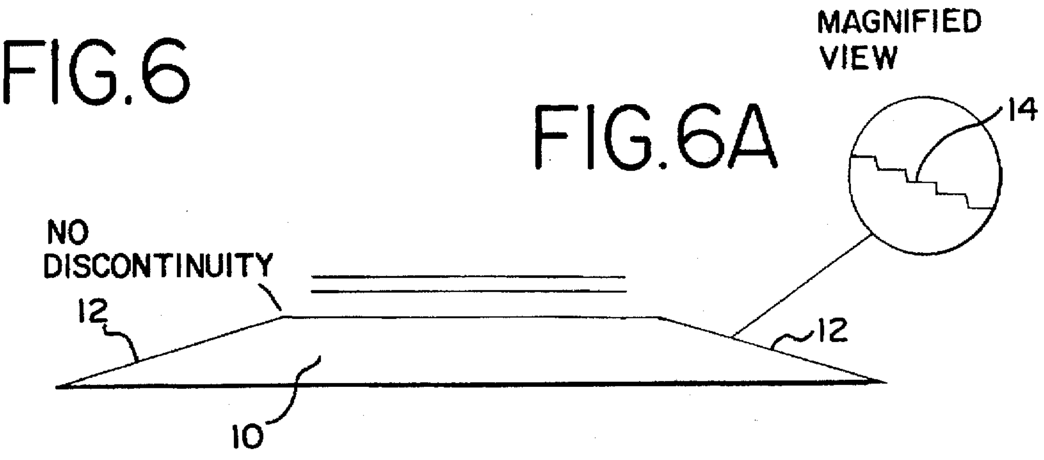
FIG. 7
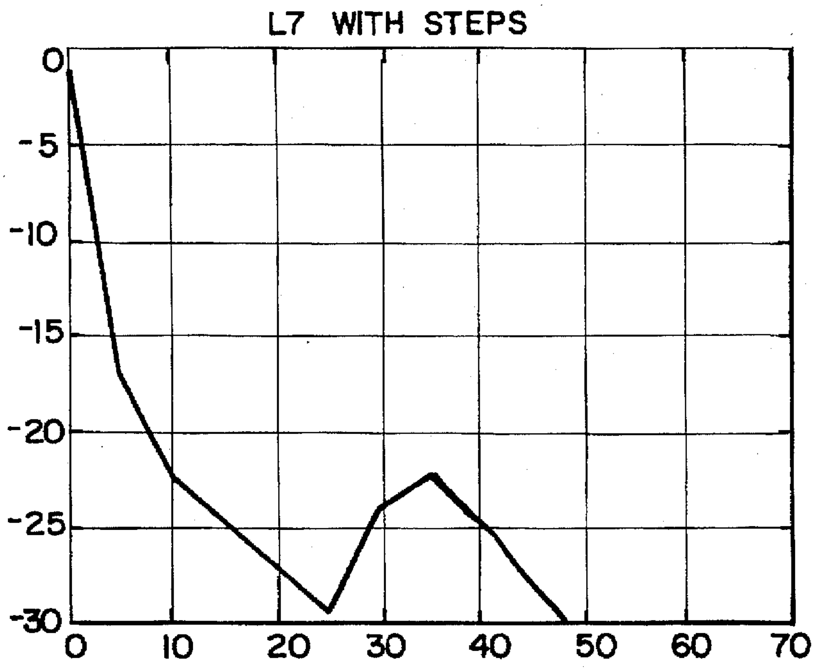
FIG.8
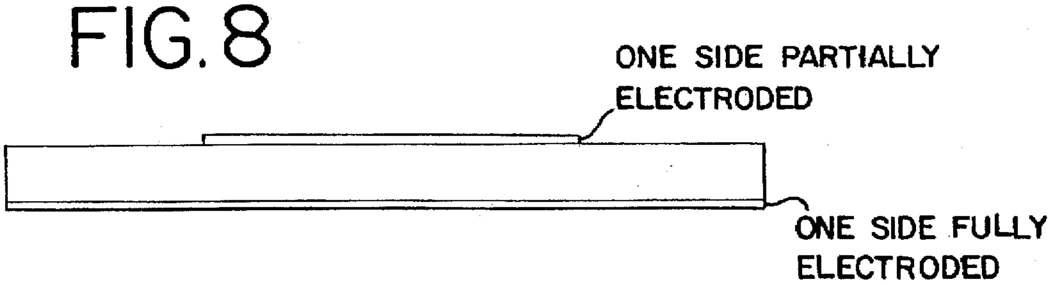

ULTRASONIC TRANSDUCER WITH REDUCED ELEVATION SIDELOBES AND METHOD FOR THE MANUFACTURE THEREOF

FIELD OF THE INVENTION

This invention relates to piezoelectric ultrasound transducers and more particularly to piezoelectric transducers in which the generation of undesirable sidelobes is controlled. The invention also relates to methods for manufacturing such piezoelectric transducers. The piezoelectric transducers of the present invention are particularly useful in medical imaging applications.

Ultrasound machines are often used for observing organs in the human body. Typically, these machines contain transducer arrays for converting electrical signals into pressure waves and vice versa. Generally, the transducer array is in the form of a hand-held probe which may be adjusted in position to direct the ultrasound beam to the region of interest.

As seen in FIGS. 1, 2 and 4, a transducer array 10 may have, for example, 128 transducer elements 12 in the azimuthal direction for generating an ultrasound beam. Adapted from radar terminology, the x, y and z directions are referred to as the azimuthal, elevation and range directions, respectively.

The transducer element 12 is typically rectangular in cross section and includes a first electrode 14, a second electrode 16, a piezoelectric layer 18 and one or more acoustic matching layers 20 and 22. The transducer elements 12 are disposed on a backing block 24. In addition, a mechanical lens 26 may be placed on the matching layers to help confine the generated beam in the y-z plane. Examples of prior art transducer structures are shown in Charles S. DeSiltes, *Transducer Arrays Suitable for Acoustic Imaging,* Ph. D. Thesis, Stanford University (1978) and Alan R. Selfridge, *Design and Fabrication of Ultrasonic Transducers and Transducer Arrays,* Ph. D. Thesis, Stanford University (1982). An example of a phased array acoustic imaging system is described in U.S. Pat. No. 4,550,607 issued Nov. 5, 1985 to Maslak et al. and is specifically incorporated herein by reference. U.S. Pat. No. 4,550,607 illustrates circuitry for combining the incoming signals received by the transducer array to produce a focused image on the display screen.

Individual elements 12 can be electrically excited by electrodes 14 and 16 with different amplitudes and phases to steer and focus the ultrasound beam in the x-z plane. Terminals 28 and 30 may be connected to each of the electrodes 14 and 16 for providing the electrical excitation of the element 12. Terminal 28 may provide the hot wire or excitation signal, and terminal 30 may provide the ground. As a result a primary wave 31 is provided in the z-direction. (see FIG. 2)

The force distribution on the face 32 of the transducer element 12 and the acoustic and geometrical parameters of the mechanical lens 26 describe the radiation pattern in the elevation direction as a function of an angle in the y-z plane. The finite width of the transducer element 12 in the y-direction causes the sides 36 and 38 of the transducer element 12 to move freely. This motion in turn creates lateral waves 40 propagating along the y-direction. These lateral waves 40 propagating though the composite structure of piezoelectric layer 18 and matching layers 20 and 22 may have a phase velocity greater than that of the external medium, i.e. the patient being examined, and may excite an undesirable secondary propagating wave and "leak" into the external medium. In addition, it has been found that lead zirconate titanate (PZT) is the most efficient piezoelectric ceramic for use in ultrasound probes. Unfortunately it has been found that the thickness mode vibrations and lateral mode vibrations are strongly coupled. This coupling gives rise to the production of lateral waves and thus undesirable elevational sidelobes.

The direction of the secondary wave in the external medium is given by the expression $\theta=\arcsin(vo/vl)$, where $\theta$ is measured with respect to the normal of the transducer face 32 in the y-z plane, vo is the velocity of the wave in the acoustic medium, and vl is the velocity of the lateral wave. This "leaky" wave will increase the sidelobe levels around the angle $\theta$. As an example, for the piezoelectric material PZT-5H, the phase velocity of the lateral wave is approximately 3,000 meters per second. This is approximately twice the phase velocity in the human body of 1,500 meters per second. Consequently, a secondary wave 42 caused by lateral wave 40 propagates at an angle $\theta$ of 30 degrees.

The sidelobe levels of individual elements of an ultrasound transducer are of particular concern in applications where a strong reflector in the object of interest, i.e. cartilage or an air pipe such as the trachea during the examination of the carotid artery, may be located outside the main acoustic beam. In such a case, the reflections from the object of interest, i.e. soft tissue, may be comparable to signals coming from a strong reflector, such as the cartilage or air pipe, outside the region of interest. As a result, the generated image is less accurate and may contain artifacts.

Referring to FIG. 3, the main, desired, lobe of a typical transducer radiation pattern 44 is shown. Due to the contribution of lateral waves, the radiation pattern outlined by region 46 results. In the absence of the lateral wave, the radiation pattern would have followed curve 48. FIG. 5 is a graph illustrating the elevational or artifact sidelobe 46 generated by a transducer element such as that illustrated in FIG. 2. The graph in FIG. 5 as well as the graphs in FIGS. 5, 7, 9, 13–16 and 17 were produced using a finite element analysis using a half cycle, 5 MHz sinusoidal excitation. The X axis represents angle in degrees and the Y axis represents decibels in dB with respect to the peak value at zero degrees. The graphs are symmetric about the Y axis with only one half of the graph illustrated in the Figures. It is seen that at 30° the sidelobe is only 15 db below the main lobe.

The radiation pattern 44 of a transducer is primarily related to the field distribution across its aperture. For continuous wave or a very narrow band excitations, the radiation pattern is related to the aperture function by the Fourier transform relationship. For wide band excitation, one may use, for example, superposition to integrate the field distributions at each frequency.

A fixed focus lens may scale the radiation pattern by modifying the phase of the aperture distribution but the general sidelobe characteristics are governed by the amplitude distribution of the aperture. In addition, apodization may be used to improve the radiation pattern by shaping the radiation distribution. Apodization results in varying the electric field between electrodes 14 and 16 along the elevation direction. However, these prior art techniques fall short because lateral waves may still be generated and contribute to undesirable sidelobe levels and may result in a less accurate image.

There have been various structures proposed to minimize the generation of sidelobes. For example, the lead titanate or PVDF may be used instead of pure PZT since these materials have less thickness to lateral vibration coupling. Such materials, however, result in compromised performance, i.e. lower sensitivity and bandwidth. Alternatively, the piezoelectric layer may be modified into a composite having PZT posts embedded in a polymer matrix. Such a structure also reduces the thickness to lateral vibration coupling. However, making an entire composite block to replace the normally single phase PZT block adds considerably to the cost and complexity of manufacturing such a transducer element.

Another method involves depoling the ends of the piezoelectric layer to make them inactive. Depoling may be accomplished by exposing the ends to high temperatures, reverse electric fields or mechanically damaging the ends. Poling and depoling ceramic is a non-linear process which is difficult to control and may lead to strains in the ceramic and subsequent cracking.

FIGS. 6 and 8 illustrate the cross section of a piezoelectric layer in the elevation direction according to prior art structures used to suppress the generation of elevational sidelobes. FIGS. 7 and 9 are graphs illustrating the effectiveness of the prior art structures shown in FIGS. 6 and 8 respectively for reducing the elevation sidelobe. U.S. Pat. No. 5,410,208 (Walters et al.), which is specifically incorporated herein by reference, discloses the structures shown in FIGS. 6 and 8. In FIG. 6 the piezoelectric layer 10 have been tapered in its end regions 12 by a plurality of steps 14 as shown in the magnified view FIG. 6*a*. Reduction of the thickness of the piezoelectric layer in the elevation direction using tapers reduces the activity in the end regions in a smooth manner. FIG. 7 illustrates the effectiveness of tapering the end regions of the piezoelectric layer. It can be seen that the elevational sidelobe at 30° is now about 22 db below the main lobe. Fabricating tapers at the ends of the piezoelectric layer, however, is an expensive and time consuming process. In FIG. 8, the electrodes at the ends of the piezoelectric layer are removed along the elevation direction so as to reduce activity in the region where the elevation sidelobe wave is initiated. FIG. 9 shows that cutting back the electrodes at the elevational ends of the transducer element does reduce the elevation sidelobe at 30° so that it is now about 22 db below the main lobe. Such a method, however, has not led to completely satisfactory results because it is believed that a small lateral wave initiated at the discontinuity at the edge of the electrode reflects off the end of the PZT bar in a coherent fashion. In the tapered device, the wave is dissipated as it travels down the taper and reflections are incoherent across the PZT bar cross-section.

Other methods also exist such as screening the ends of the piezoelectric layer in the elevation direction with a very high loss blocking material such as that described in U.S. Pat. No. 5,285,789 to Chen which is specifically incorporated herein by reference. Finding a material that possesses the necessary high attenuation and which is also compatible in terms of manufacturing processes and reliability is difficult. In addition, screening the end areas implies that the dimension of the transducer element in the elevation direction must be bigger than it would have if no screening was employed. This is contrary to the goal of making the physical dimensions of the transducer array as small as possible. More particularly, it is desirable to make the physical dimension of the transducer element in the elevation direction as close as possible to its active aperture. This provides greater flexibility in using the transducer array in many more locations while creating comfort to the patient.

It is thus desirable to provide a transducer structure which effectively reduces the generation of sidelobes and thereby increases imaging accuracy.

It is also desirable to provide a transducer structure which effectively reduces the generation of sidelobes simply and is inexpensive to implement.

It is desirable to provide a transducer structure that effectively reduces the generation of sidelobes while minimizing the physical dimensions of the transducer structure.

SUMMARY OF THE INVENTION

According to a first aspect of the present invention there is provided a ultrasound transducer designed to reduce the generation of elevational sidelobes in the emitted beam. The ultrasound transducer includes a body of piezoelectric material having a width along an elevation direction and a thickness along a range direction. The transducer element has a center portion with a first width, a first end region adjacent in the elevation direction to one end of the center portion and a second end region adjacent in the elevation direction to an opposite end of the center portion. The first and second end regions each has a second width smaller than the first width of the center portion. At least a first kerf extending parallel to azimuthal direction near the ends of the PZT bar in the elevational dimension and extends, in depth, in the range direction into the piezoelectric material is formed in the first end region. At least a second kerf direction is formed in the second end region and extending parallel to azimuthal direction near the ends of the PZT bar in the elevational dimension and extends, in depth, in the range direction into the piezoelectric material. A second material fills the first and second kerfs while the center portion is formed solely of piezoelectric material.

According to a second aspect of the present invention there is provided an ultrasound transducer element for reducing the generation of elevational sidelobes. The transducer includes a layer of ceramic having a top surface, a bottom surface, a first side surface and a second side surface. The top and bottom surfaces define a width of the layer along an elevation direction and the first and second side surfaces define a thickness of the layer along a range direction. A first electrode is coupled to the top surface of the layer. A second electrode is coupled to the bottom surface of the layer. The layer of ceramic is composed of pure PZT over a first percentage and a composite PZT over a second percentage the first percentage being greater than the second percentage.

According to a third aspect of the present invention there is provided a method of making a transducer element which reduces the generation of elevational sidelobes. The method includes providing a body of piezoelectric material having a width along an elevation direction and a thickness along a range direction, the body having a center portion having a first width and a first and second end regions having a second width; the first width being greater than the second width; dicing a first kerf in the first end region, dicing a second kerf in the second end region; and filling the first and second kerfs with a second material.

The invention itself, together with further objects and attendant advantages, will best be understood by reference to the following detailed description, taken in conjunction with the accompanying drawings.

BRIEF DESCRIPTION OF THE DRAWINGS

FIG. 6 illustrates the cross section of a piezoelectric layer in the elevation direction according to prior art structure used to suppress the generation of elevational sidelobes by tapering the elevational sides of the piezoelectric layer.

FIG. 7 is a graph illustrating the effectiveness of the prior art structure shown in FIG. 6 for reducing the elevation sidelobe.

FIG. 8 illustrates the cross section of a piezoelectric layer in the elevation direction according to prior art structures used to suppress the generation of elevational sidelobes by partially removing the top electrode.

DETAILED DESCRIPTION OF THE PRESENTLY PREFERRED EMBODIMENTS

Figure 10:
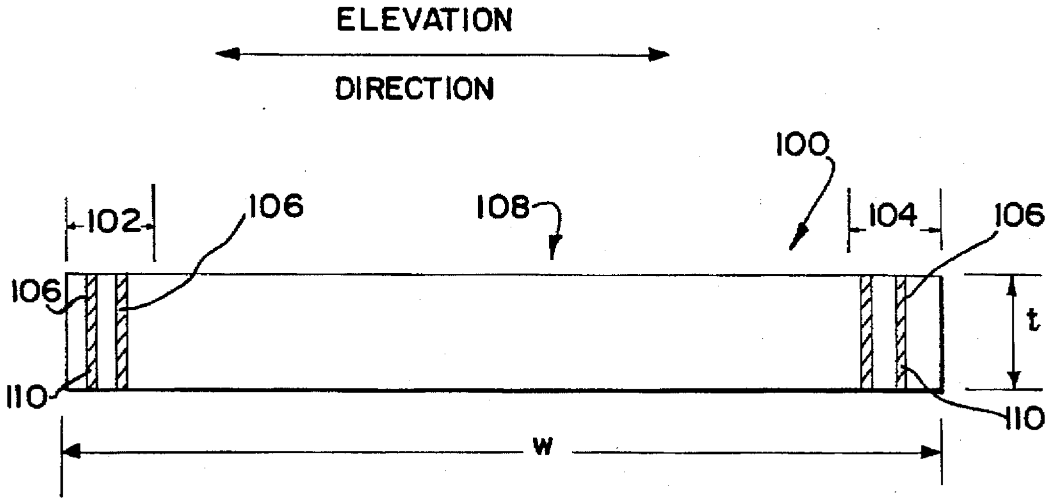
FIG. 10 illustrates a layer of piezoelectric material according to a first preferred embodiment of the present invention.

FIG. 10 illustrates a layer of piezoelectric material according to a first preferred embodiment of the present invention. The layer of piezoelectric material 100 has a width w extending in an elevation direction and a thickness t extending in a range direction. The width w of the layer is greater than its thickness t. In a preferred embodiment, the ratio of the layer's width to its thickness is about 30:1. The layer 100 is formed from a body of piezoelectric material. In a first end region 102 and a second end 104 region kerfs 106 are diced into the body of piezoelectric material. A center region 108 is defined between the first and second end regions 102 and

104 respectively. The center region 108 is formed solely of PZT. In this particular embodiment, two kerfs 106 have been formed in each end region, however, more or less than two may be formed in the ends regions and the present invention is not limited to the particular embodiment illustrated. The kerfs 106 formed in the end regions are filled with a second material 110 different from the piezoelectric layer 100, preferably an epoxy. Alternatively, the filler may be a particle filled epoxy, for example, alumina, tungsten, tungsten oxide, lead oxide, and silica. Even glass or plastic microballoon or microsphere filled epoxy may be used. Such microballoons or microspheres are commercially available from Polysciences of Warrington, Pa. The kerfs may be formed using a dicing blade or laser such as a $CO_2$ or excimer laser as is well known in the art.

These kerfs create abrupt transitions in acoustic properties in the transducer element, and therefore give rise to internal reflections of any lateral waves that may be generated in the material. By careful selection of the spacing of the kerfs, these internal reflections may be made to provide maximum destructive interference in a laterally propagated wave. An optimum selection of kerf spacing and number of kerfs may be determined by experimentation or by using finite element analysis. As an example, quarter wavelength center-to-center spacing, calculated using the center frequency of the transducer and the speed of the laterally propagating wave, may give an optimal result.

Figure 11:
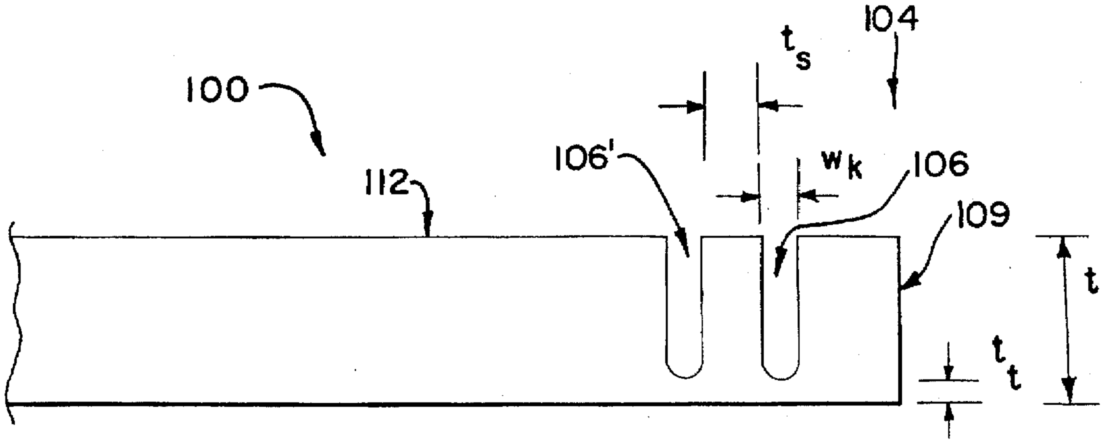
FIG. 11 illustrates the right half of the layer of piezoelectric material shown in FIG. 10 in greater detail with the composite material.

FIG. 11 illustrates the right half of the layer of piezoelectric material 100 shown in FIG. 10 in greater detail without the second material filling the kerfs 106. A layer of piezoelectric material was actually fabricated to have the following dimensional characteristics. The layer 100 had a width w (see FIG. 10) in the elevation direction of about 4 mm and a thickness t in the range direction of 130 μm. Two kerfs 106 were diced in the second end region 104 of the body of piezoelectric material. The kerfs 106 extend, in depth in the range direction and have a depth from the top surface 112 of the piezoelectric body of about 105 μm thereby leaving a thickness $t_r$ of 25 μm under the kerfs 106. Of course in a transducer array a plurality of transducer elements would be positioned one behind the other in the azimuthal direction. The kerfs formed in the elevational end regions of the transducer segments would extend parallel to the azimuthal direction. Alternatively, the depth of the kerfs may extend completely through the piezoelectric layer 100 or only partially through, for example from about 10% to 90%. The kerfs 106 were diced having a width $w_K$ in the elevation direction of about 25 μm and a separation $t_s$ between the kerf 106' and kerf 106 of about 75 μm. The pitch from the center of kerf 106' to the center of the adjacent kerf 106 is about 100 μm. The distance from the center of kerf 106' to the edge 109 of the piezoelectric layer 100 is about 0.1875 mm.

In another preferred embodiment a layer of piezoelectric material having a small width of 1 mm in the elevation direction may be constructed. If two kerfs are formed in each end region where the center-to-center spacing between adjacent kerfs is 100 μm, the center region is about 0.6 mm wide and formed of solid PZT.

In a preferred embodiment the following materials were used. The body of piezoelectric material 100 was formed of D3203HD commercially available from Motorola Ceramic Products of Albuquerque, N. Mex. PZT-5H commercially available from Morgan Matroc, Inc., of Bedford, Ohio could also be used. The second material (see FIG. 10) filling the kerfs 106' and 106 formed in the end regions of the body of piezoelectric material was preferably a polymer RE2039 with hardener HD3561 commercially available from Hysol of Industry, Calif.

Figure 12:
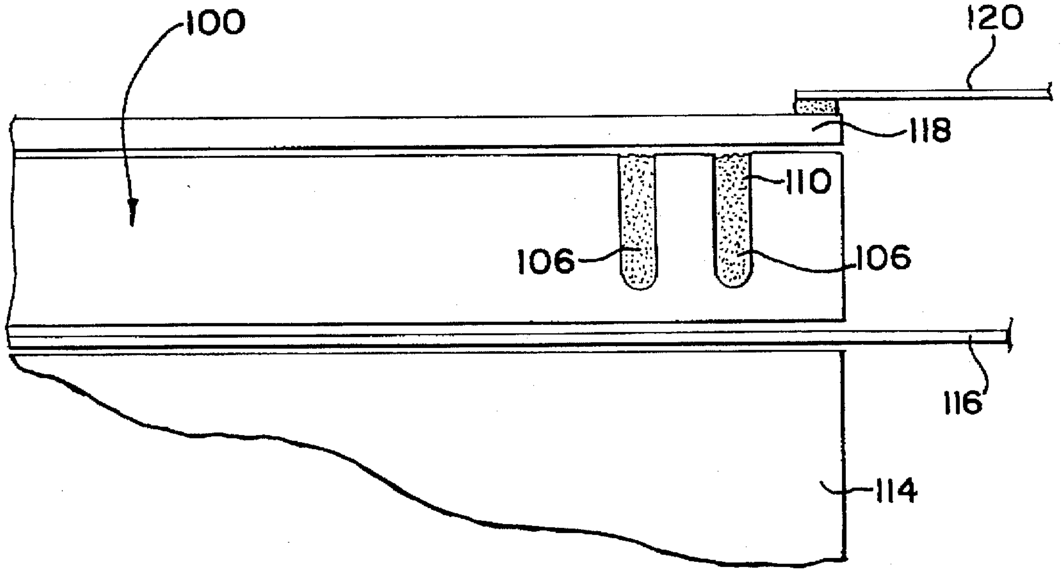
FIG. 12 illustrates a cross-sectional view of a transducer array in the elevational direction.

FIG. 12 illustrates a cross-sectional view of a transducer array in the elevational direction. In a preferred embodiment, the transducer array includes the layer of piezoelectric material 100 with a plurality of kerfs 106 filled with a second material 110 in the end regions of the body as shown in FIG. 10. A support member 114 in the form of a backing block is provided with a copper flex circuit 116 disposed thereon. The piezoelectric assembly 100 is disposed on top of the flex circuit 116. An acoustic matching layer 118, preferably metalized is disposed above the piezoelectric assembly 100. In a preferred embodiment, the acoustic matching layer 118 is formed of an alumina filled epoxy. More than one acoustic matching layer may be provided. A ground electrode 120 is coupled to the ends of the acoustic matching layer 118. While there appears to be space between the various elements, there is contact between the elements. The matching layer 118 is metalized on all surfaces so that it electrically couples the ground electrode 120 to the top surface of the piezoelectric material 100. In addition, the metalized matching layer 118 bridges over the kerfs to electrically couple the center region 108 of the piezoelectric layer 100 to the ground electrode 120 which is coupled to the metalized matching layer 118 at its ends.

Figure 13:
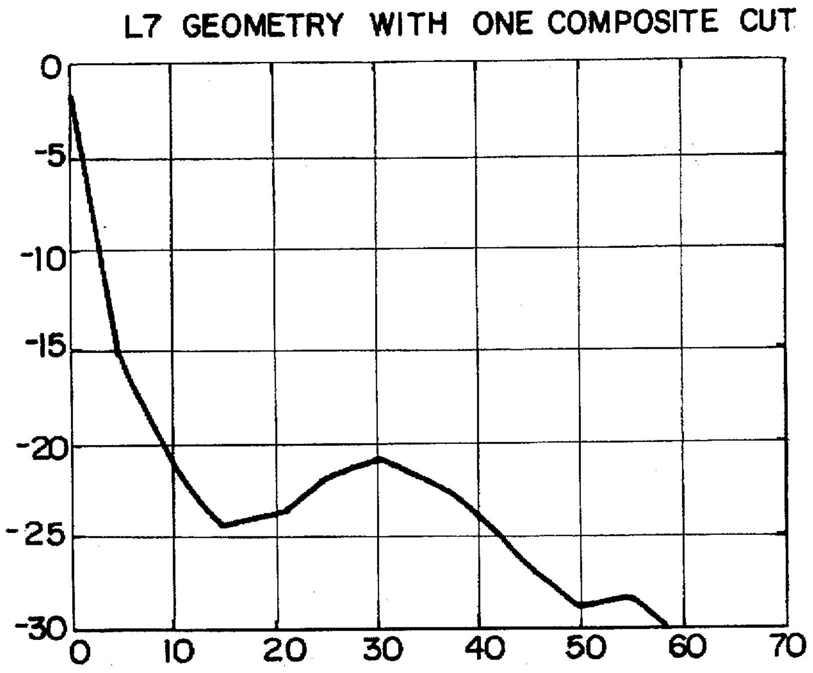
FIG. 13 is a graph illustrating the effectiveness in the reduction of the generation of elevational sidelobe for a transducer element formed according to the present invention having only one kerf formed in each end region of the body of piezoelectric material.

FIG. 13 is a graph illustrating the effectiveness in the reduction of the generation of elevational sidelobe for a transducer element formed according to the present invention having only one kerf formed in each end region of the body of piezoelectric material. It can be seen that the elevational sidelobe located at an angle of 30° is about 22 db lower than the main lobe centered around the origin.

Figure 14:
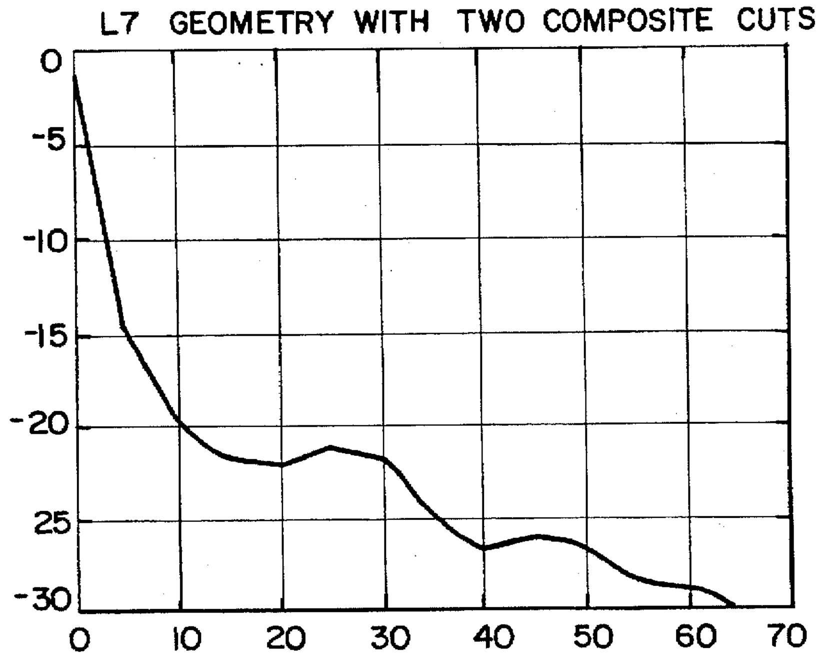
FIG. 14 is a graph illustrating the effectiveness in the reduction of the generation of elevational sidelobe of a transducer element formed according to the present invention having two kerfs formed in each end region of the body of piezoelectric material, such as that illustrated in FIG. 10.

FIG. 14 is a graph illustrating the effectiveness in the reduction of the generation of elevational sidelobe of a transducer element formed according to the present invention having two kerfs formed in each end region of the body of piezoelectric material, such as that illustrated in FIG. 10. It can be seen that the elevational sidelobe located at an angle of 25° is about 22 db lower than the main lobe centered around the origin.

Figure 15:
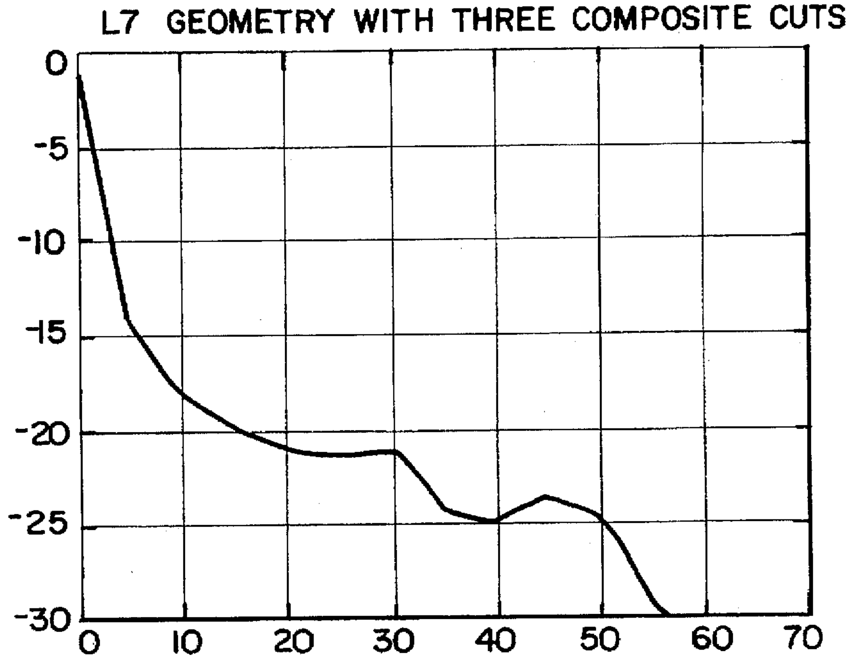
FIG. 15 is a graph illustrating the effectiveness in the reduction of the generation of elevational sidelobe of a transducer element formed according to the present invention having three kerfs formed in each end region of the body of piezoelectric material.

FIG. 15 is a graph illustrating the effectiveness in the reduction of the generation of elevational sidelobe of a transducer element formed according to the present invention having three kerfs formed in each end region of the body of piezoelectric material. It can be seen that the elevational sidelobe located at an angle of 30° is about 22 db lower than the main lobe centered around the origin.

Figure 16:
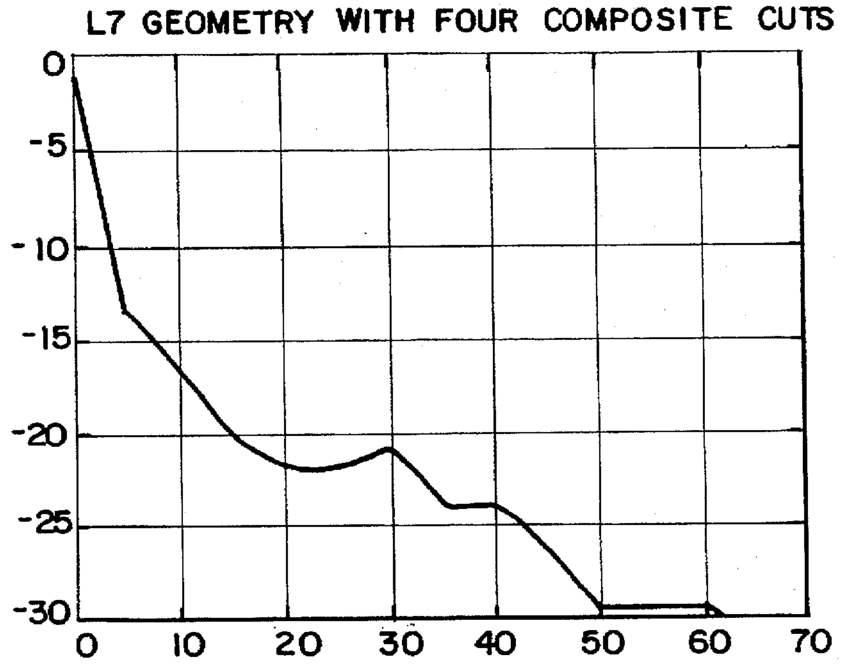
FIG. 16 is a graph illustrating the effectiveness in the reduction of the generation of elevational sidelobe of a transducer element formed according to the present invention having four kerfs formed in each end region of the body of piezoelectric material.

FIG. 16 is a graph illustrating the effectiveness in the reduction of the generation of elevational sidelobe of a transducer element formed according to the present invention having four kerfs formed in each end region of the body of piezoelectric material. It can be seen that the elevational sidelobe located at an angle of 30° is about 22 db lower than the main lobe centered around the origin.

When a plurality of kerfs are formed in the end regions of the piezoelectric material, the spacing between the kerfs does not have to be uniform but rather can be made non-uniform to produce optimum results. In addition, the depths of the kerfs do not have to be uniform.

Figure 1:
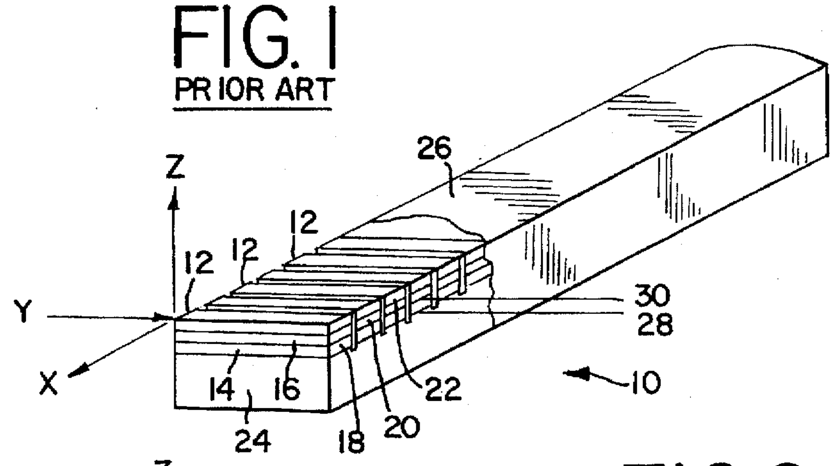
FIG. 1 PRIOR ART
FIG. 1 is a perspective view of a transducer array according to the prior art.
Figure 2:
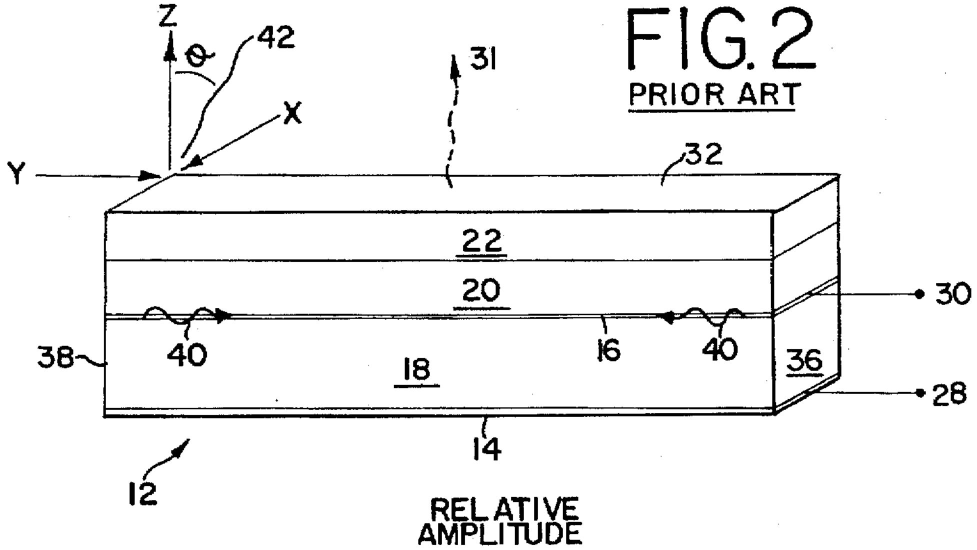
FIG. 2 PRIOR ART
FIG. 2 is a cross sectional view of the transducer array shown in FIG. 1 taken along the elevational direction illustrating the secondary wave phenomenon.
Figure 3:
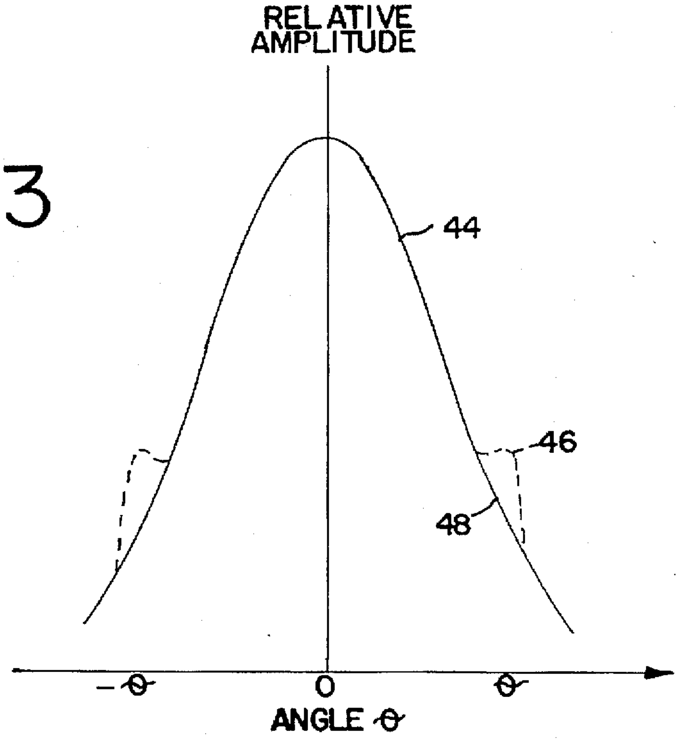
FIG. 3 is a beam plot illustrating the elevational sidelobes.
Figure 4:
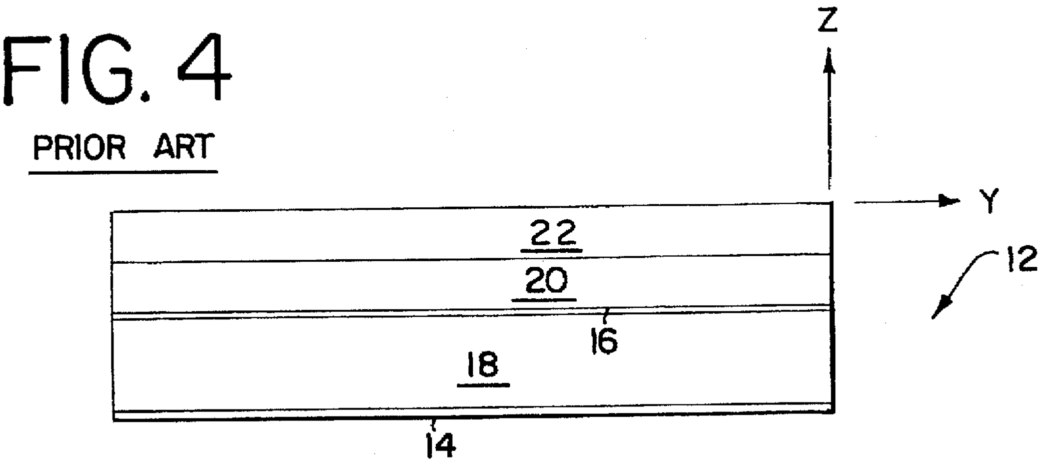
FIG. 4 PRIOR ART
FIG. 4 is a cross-sectional view of a transducer element shown in FIG. 1.
Figure 5:
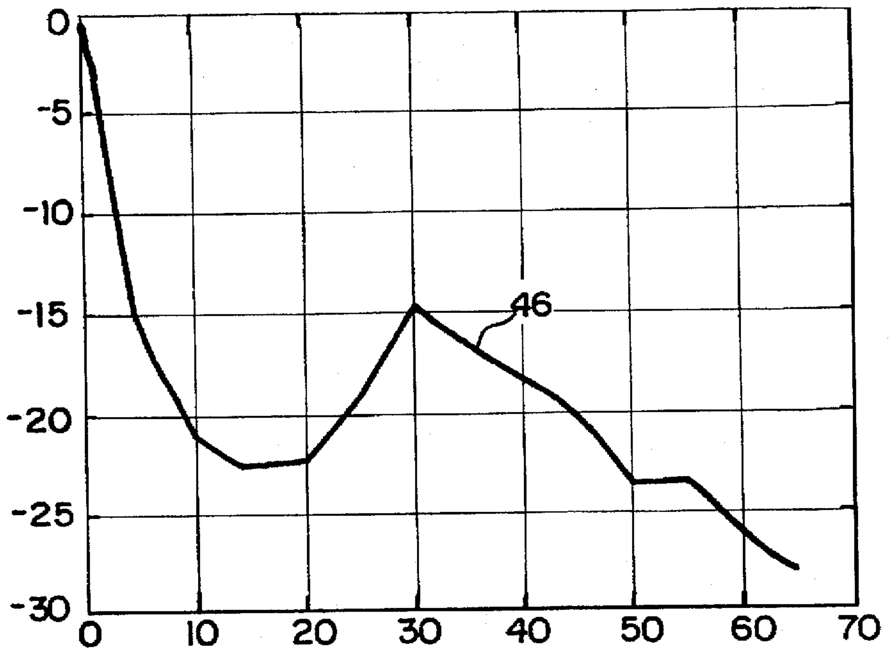
FIG. 5 is a graph illustrating the elevational sidelobe generated by a transducer element such as that illustrated in FIG. 2.
Figure 9:
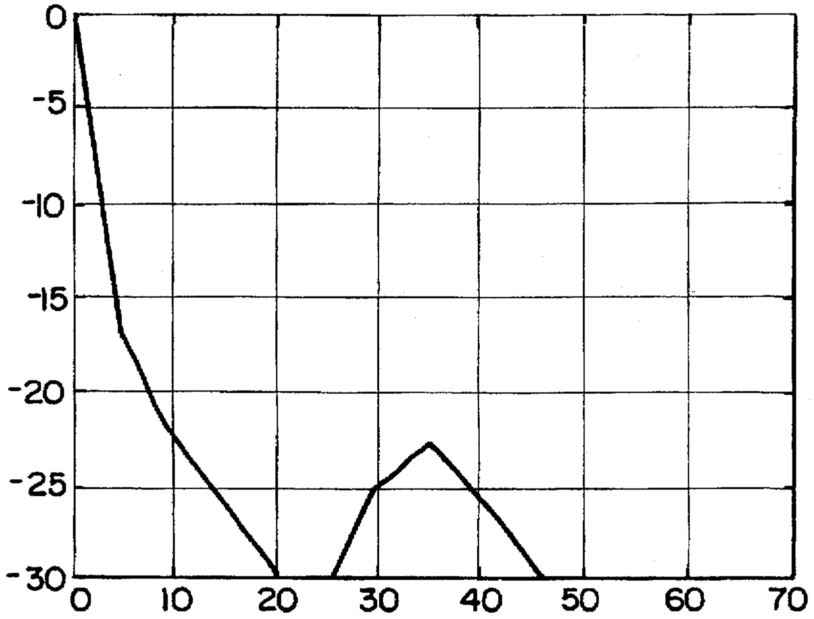
FIG. 9 is a graph illustrating the effectiveness of the prior art structure shown in FIG. 8 for reducing the elevation sidelobe.
Figure 17:
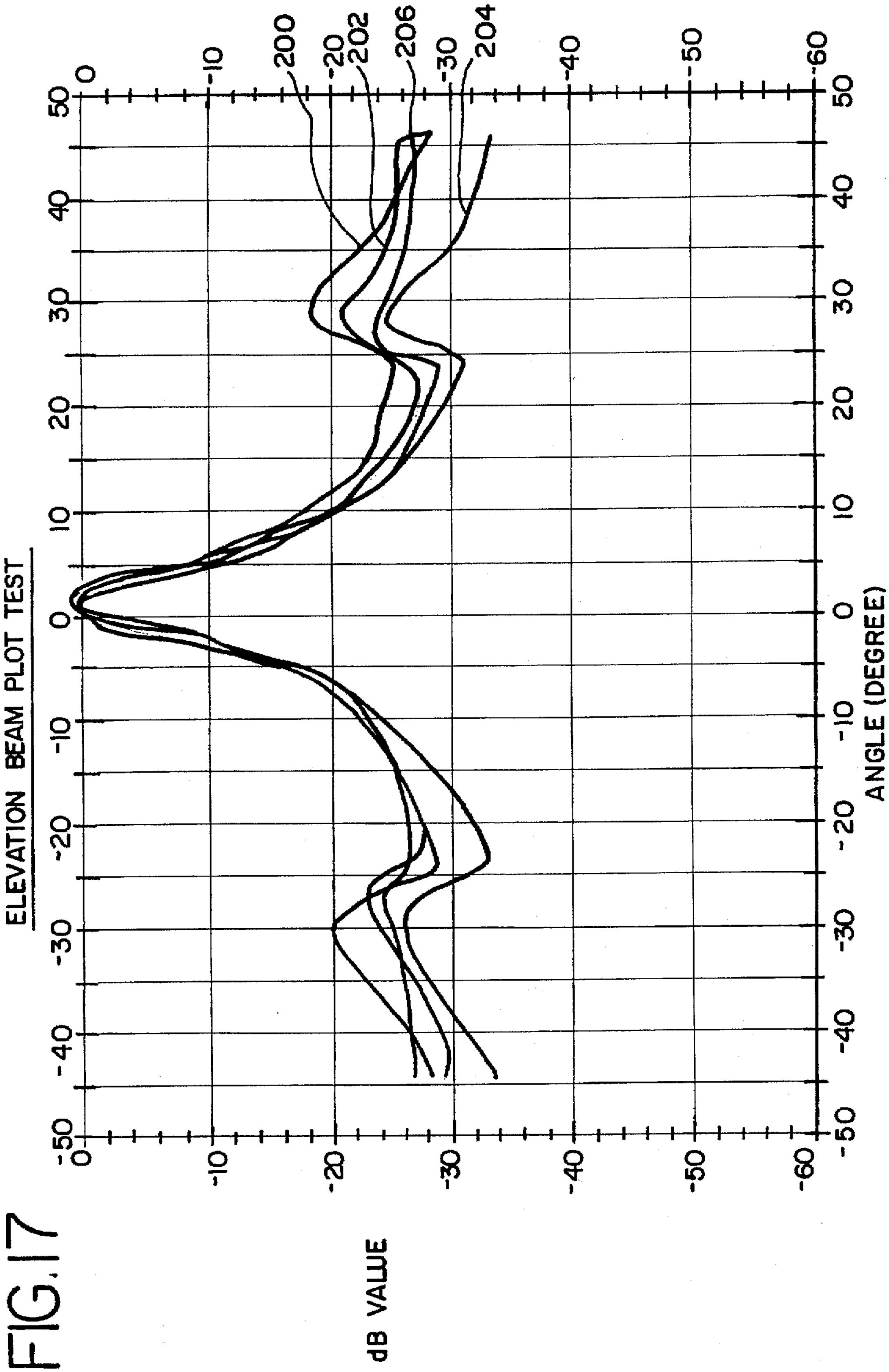
FIG. 17 is an elevational beam plot comparing the beam plots for transducer arrays according to the prior art as well as those according to the present invention.

FIG. 17 is an elevational beam plot comparing the beam plots for transducer arrays according to the prior art as well as those according to the present invention. The db value is on the vertical axis and the angle in degrees is on the horizontal axis. Plot 200 illustrates the beam plot for a transducer element in which no modification has been made to reduce the generation of elevational sidelobes. Plot 202 illustrates the beam plot for a transducer element such as that shown in FIG. 5 where the piezoelectric layer has been modified by tapering the sides of the layer. Plot 204 illustrates the beam plot for a transducer element modified according to the present invention having two kerfs filled with a second material formed in each end region of the body of piezoelectric material. Plot 206 illustrates the beam plot for a transducer element modified according to the present invention having four kerfs filled with a second material formed in each end region of the body of piezoelectric material.

It can be seen that the most effective reduction in elevational sidelobe was achieved using the layer of piezoelectric material having two kerfs filled with a second material in each end region of the body of piezoelectric material.

The present invention is particularly beneficial in reducing the generation of elevational sidelobes for 1.5D and 2.0D transducer arrays. This is true because the transducer elements in such arrays are typically short in length in the elevational direction. For example, a 10 mm aperture may be implemented by 5, 2 mm long transducer segments. Since the elevational or artifact sidelobe is independent, to a large extent, of elevational length of the transducer segment but the main, desired lobe is a function of elevational length, the shorter transducer segments are more prone to exhibiting the artifact sidelobe problem. Implementing the present invention in such transducer arrays will help reduce the generation of the undesired elevational side lobe.

A transducer element produced according to the present invention has other advantages over composite type transducer elements which are 50% PZT throughout the transducer element. A transducer element produced according to the present invention, for example, one that is 100% PZT over 90% of the element and 50% PZT over the remaining 10% has a higher capacitance and thus better electrical match and higher sensitivity than a composite transducer element that is 50% throughout the element. In addition, the cost and time involved in manufacturing a transducer element according to the present invention is considerably reduced compared to other methods of reducing the generation of elevational sidelobes.

It is to be understood that the forms of the invention described herewith are to be taken as preferred examples and that various changes in the shape, size and arrangement of parts may be resorted to, without departing from the spirit of the invention or scope of the claims.

What is claimed is:

1. An ultrasound transducer designed to reduce the generation of elevational sidelobes, the transducer comprising:

a body of piezoelectric material having a width along an elevation direction and a thickness along a range direction, said transducer element having a center portion having a first width, said center portion formed solely of piezoelectric material the center portion having a width in the elevation direction and thickness in the range direction wherein the width is at least four times greater than the thickness, a first end region adjacent in the elevation direction to one end of said center portion and a second end region adjacent in the elevation direction to an opposite end of said center portion, said first and second end regions each having a second width in the elevation direction wherein said first width is greater than said second width;

at least a first kerf formed in said first end region, said first kerf extending, in depth, in the range direction to a first depth; and at least a second kerf formed in said second end region, said second kerf extending, in depth, in said range direction to a second depth; and a second material disposed in said first kerf and said second kerf.

2. An ultrasound transducer according to claim 1 wherein said second material comprises an epoxy.

3. An ultrasound transducer according to claim 1 wherein said first and said second kerfs have a width in the elevation direction of about 25 μm.

4. An ultrasound transducer according to claim 1 further comprising one or more additional kerfs formed in said first and second end regions.

5. An ultrasound transducer according to claim 4 wherein said plurality of kerfs may range from two to four.

6. An ultrasound transducer according to claim 5 wherein the distance between the center of a kerf to the center of the next adjacent kerf is a quarter wavelength of the center frequency of the transducer.

7. An ultrasound transducer according to claim 4 wherein said plurality of kerfs comprises two.

8. An ultrasound transducer according to claim 1 further comprising:

a backing block;

a flex circuit disposed on said backing block, said body of piezoelectric material disposed on said flex circuit;

an electrode disposed above said body of piezoelectric material; and at least a first layer of acoustic matching material disposed over said electrode.

9. An ultrasound transducer according to claim 1 wherein said body of piezoelectric material has a thickness of about 130 μm and said first and second depths of said first and said second kerfs is about 105 μm.

10. An ultrasound transducer according to claim 1 wherein said first and second kerfs extend more than 50% through said body of piezoelectric material.

11. An ultrasound transducer according to claim 4 wherein said kerfs are not uniformly spaced.

12. An ultrasound transducer element designed to reduce the generation of elevational sidelobes, the transducer element comprising:

a layer of ceramic having a top surface, a bottom surface, a first edge and a second edge, said top and bottom surfaces defining a width of said layer along an elevation direction and said first and second edges defining a thickness of said layer along a range direction;

a first electrode coupled to said top surface of said layer; and a second electrode coupled to said bottom surface of said layer, wherein said layer of ceramic is composed of pure PZT over a center region, said center region having a width along the elevation direction and a thickness along the range direction wherein the width of the center region is greater than its thickness and a composite PZT in end regions on opposite sides of said center region wherein said end regions has a second width, said first width being greater than said second width.

13. An ultrasound transducer according to claim 12 wherein said ratio of said width of said region to said second width is about 9:1.

14. An ultrasound transducer according to claim 12 wherein said ratio of said width of said center region to said second width is greater than 2:1.

15. An ultrasound transducer according to claim 12 wherein said composite PZT is formed by epoxy filled kerfs formed in said layer of ceramic.

16. An ultrasound transducer according to claim 12 wherein said first width is greater than said thickness of said layer.

17. An ultrasound transducer according to claim 16 wherein said first width is at least twice as great as said thickness.

18. A method of making a transducer element designed to reduce the generation of elevational sidelobes, the method comprising the steps of:

providing a body of piezoelectric material having a width along an elevation direction and a thickness along a range direction, said body having a center portion having a first width in the elevation direction and a first thickness in the range direction wherein the first width is at least four greater than the first thickness, and a first and second end regions located at opposite ends of the center portion, the second end regions having a second width, said first width being greater than said second width;

dicing a first kerf in said first end region;

dicing a second kerf in said second end region; and filling said first and second kerfs with a second material.

19. A method according to claim 18 further comprising the steps of dicing a plurality of kerfs in said first and said second end regions and filling said plurality of kerfs with said second material.

20. A method according to claim 19 wherein said second material is an epoxy.

21. A method according to claim 19 wherein said plurality of kerfs comprises four.

22. An ultrasound transducer designed to reduce the generation of elevational sidelobes, the transducer comprising:

a body of piezoelectric material having a width along an elevation direction and a thickness along a range direction, said transducer element having a center portion having a first width, said center portion formed solely of piezoelectric material the center portion having a width in the elevation direction and thickness in the range direction wherein the width is greater than the thickness, a first end region adjacent in the elevation direction to one end of said center portion and a second end region adjacent in the elevation direction to an opposite end of said center portion, said first and second end regions each having a second width in the elevation direction wherein said first width is greater than said second width and wherein the center portion comprises at least 60% of said transducer element;

at least a first kerf formed in said first end region, said first kerf extending, in depth, in the range direction to a first depth; and at least a second kerf formed in said second end region, said second kerf extending, in depth, in said range direction to a second depth; and a second material disposed in said first kerf and said second kerf.

23. A method of making a transducer element designed to reduce the generation of elevational sidelobes, the method comprising the steps of:

providing a body of piezoelectric material having a width along an elevation direction and a thickness along a range direction, said body having a center portion having a first width in the elevation direction and a first thickness in the range direction wherein the first width is greater than the first thickness, and a first and second end regions located at opposite ends of the center portion, the second end regions having a second width, said first width being greater than said second width and wherein the center portion comprises at least 60% of said transducer element;

dicing a first kerf in said first end region;

dicing a second kerf in said second end region: and filling said first and second kerfs with a second material.

* * * * *

UNITED STATES PATENT AND TRADEMARK OFFICE

CERTIFICATE OF CORRECTION

PATENT NO. : 5,706,820

DATED : January 13, 1998

INVENTOR(S) : John A. Hossack et al.

It is certified that error appears in the above-indentified patent and that said Letters Patent is hereby corrected as shown below:

In column 2, line 42, replace "dB" with --db--.

In column 3, line 25, replace "have" with --has--.

In column 6, line 4, replace "ends" with --end--.

Signed and Sealed this

Sixth Day of April, 1999

Attest:

Q. TODD DICKINSON

Attesting Officer

Acting Commissioner of Patents and Trademarks